United States Patent [19]
Arkans

[11] 4,331,133
[45] May 25, 1982

[54] PRESSURE MEASUREMENT APPARATUS

[75] Inventor: Edward J. Arkans, Hoffman Estates, Ill.

[73] Assignee: The Kendall Company, Walpole, Mass.

[21] Appl. No.: 164,136

[22] Filed: Jun. 30, 1980

[51] Int. Cl.³ .............................................. A61F 5/04
[52] U.S. Cl. ................................ 128/87 R; 73/712; 128/DIG. 20
[58] Field of Search ................... 128/675, 32.1, 30, 90, 128/30.2, 60, 24 R, 85, 87 R, 87 A, DIG. 20, 38, 66, 370, 677, 679–686, 694; 73/700, 712; D24/64

[56] References Cited

U.S. PATENT DOCUMENTS

| | | | |
|---|---|---|---|
| 1,089,122 | 3/1914 | Faught | 128/677 |
| 2,113,253 | 4/1938 | Gary | 128/66 |
| 2,699,165 | 1/1955 | Ferrier | 128/60 |
| 2,823,668 | 2/1958 | Van Court et al. | 128/87 |
| 2,826,191 | 3/1958 | Burns | 128/682 |
| 3,143,111 | 8/1964 | Green | 128/683 |
| 3,371,661 | 3/1968 | Budde | 128/680 |
| 3,416,516 | 12/1968 | Cohen et al. | 128/686 |
| 3,570,474 | 3/1971 | Jonson et al. | 128/694 |
| 4,039,039 | 8/1977 | Gottfried | 128/87 |
| 4,206,764 | 6/1980 | Williams et al. | 128/677 |

Primary Examiner—Richard C. Pinkham
Assistant Examiner—T. Brown
Attorney, Agent, or Firm—James W. Potthast

[57] ABSTRACT

A method of determining the pressure applied to a limb by an inflatable garment by placing a flexible pressurizable cuff between the garment and the limb to receive the compressive garment forces and then determining the pressure in the cuff due to those compressive forces alone. The cuff pressure component due to compression of the garment is determined by extra-polating from a plot of cuff pressure versus bias pressure. The bias pressure is required to obtain an accurate reading of cuff pressure and is eliminated as a component in determining the garment pressure by means of the extrapolation. A preferred transducer for converting cuff pressure to electrical signals employs a manometer tube extending between two plates of a capacitor.

13 Claims, 4 Drawing Figures

PRESSURE MEASUREMENT APPARATUS

BACKGROUND OF THE INVENTION

This invention relates to pressure measurement apparatus and methods generally and particularly for use in determining the pressure applied by an inflatable or elastic garment to an injured part of a patient's body.

Inflatable splints or other inflatable garments have become a convenient means for keeping broken bones immobile and for the treatment of other conditions such as prevention of deep vein thrombosis, edema and venous ulcers. The pressure applied to the injured area by the garment depends on the extent of inflation of the garment itself. If the pressure is too great, the blood circulation to the limb can be adversely affected and if the pressure in the garment is too little, the garment becomes ineffective as a splint. It is therefore necessary that the pressure applied by the garment be measured.

A known way of measuring the pressure in the inflatable garments has been to measure it directly with measurement devices built into the garment itself. Examples of such devices are shown in U.S. Pat. Nos. 2,823,668; 2,699,165; 2,113,253; and 4,039,039.

For purposes of economy and easy storage many other inflatable garments have no built-in pressure measuring systems. These garments are manufactured in a fully sealed condition, such that the subsequent application of a direct measuring device to the garment itself is not practical. Accordingly, in the past, the judgment of the person inflating such garments had to be relied upon to determine the correct amount of pressure. Such judgment is not always adequate, such that the desired result is not achieved because of inadequate pressure or circulation is impaired and the patient suffers discomfort or further injury because of too much pressure.

SUMMARY OF THE INVENTION

It is, therefore, the principal object of this invention to provide apparatus for indirectly measuring the pressure of an inflatable garment of the type which does not have built-in pressure measurement means.

In accordance with this objective, a flexible, pressurizable member, or cuff, is placed between the injured limb and the garment and is compressed therebetween by the garment pressure. The pressure in the cuff, due to compression which is approximately equal to the pressure applied to the limb by the garment, is then determined.

A minimum amount of bias pressure is needed for the cuff pressure measuring means to operate accurately. The cuff pressure, therefore, has two components: the necessary bias pressure from the injected air and the compressive pressure due to the garment pressing in on the cuff and tending to reduce its volume. The cuff is provided with means for injecting the cuff with a known amount of gas, preferably air, to produce a known bias pressure therein and means for measuring the total pressure in the cuff, or cuff pressure. Varying amounts of bias pressure are produced which results in corresponding varying amounts of total cuff pressure. Both of these are measured, and from these measurements the components of total cuff pressure due to garment compression alone, i.e., the theoretical total cuff pressure when thee is a complete absence of bias pressure, is determined by extrapolation to zero bias pressure.

The extrapolation is performed in two ways. In one embodiment the bias pressure and total cuff pressure are converted to electrical signals and supplied to the x and y inputs, respectively, of an x-y chart recorder while bias pressure is varied. This produces a plot of cuff pressure versus bias pressure, and the extrapolation is done graphically. In another embodiment the formula for total cuff pressure is determined and solved for zero bias pressure by a suitable microcomputer.

The amount of bias pressure is estimated by measuring the amount of gas injected into the cuff. Thus, an important feature is the provision of apparatus for injecting known amounts of gas into the cuff and means for measuring such amounts and producing an electrical signal representative thereof.

The accurate measurement of the total cuff compression is important in determining the garment compressive forces, and, in keeping with another aspect of the invention, a pressure transducer is provided with an electrical circuit having a reactive impedance element which produces an input signal that varies proportionately with the impedance of the element, and means for varying the impedance in accordance with variations of pressure. A particularly advantageous feature of the preferred embodiment of the transducer is that a manometer is used to vary the impedance.

DESCRIPTION OF THE DRAWINGS

The foregoing objects, features and advantages will be explained in greater detail and further features and advantages will be made apparent from the following description of the preferred embodiment given with reference to the below described drawings and the claims.

In the drawings.

DESCRIPTION OF THE PREFERRED EMBODIMENT

Figure 1:
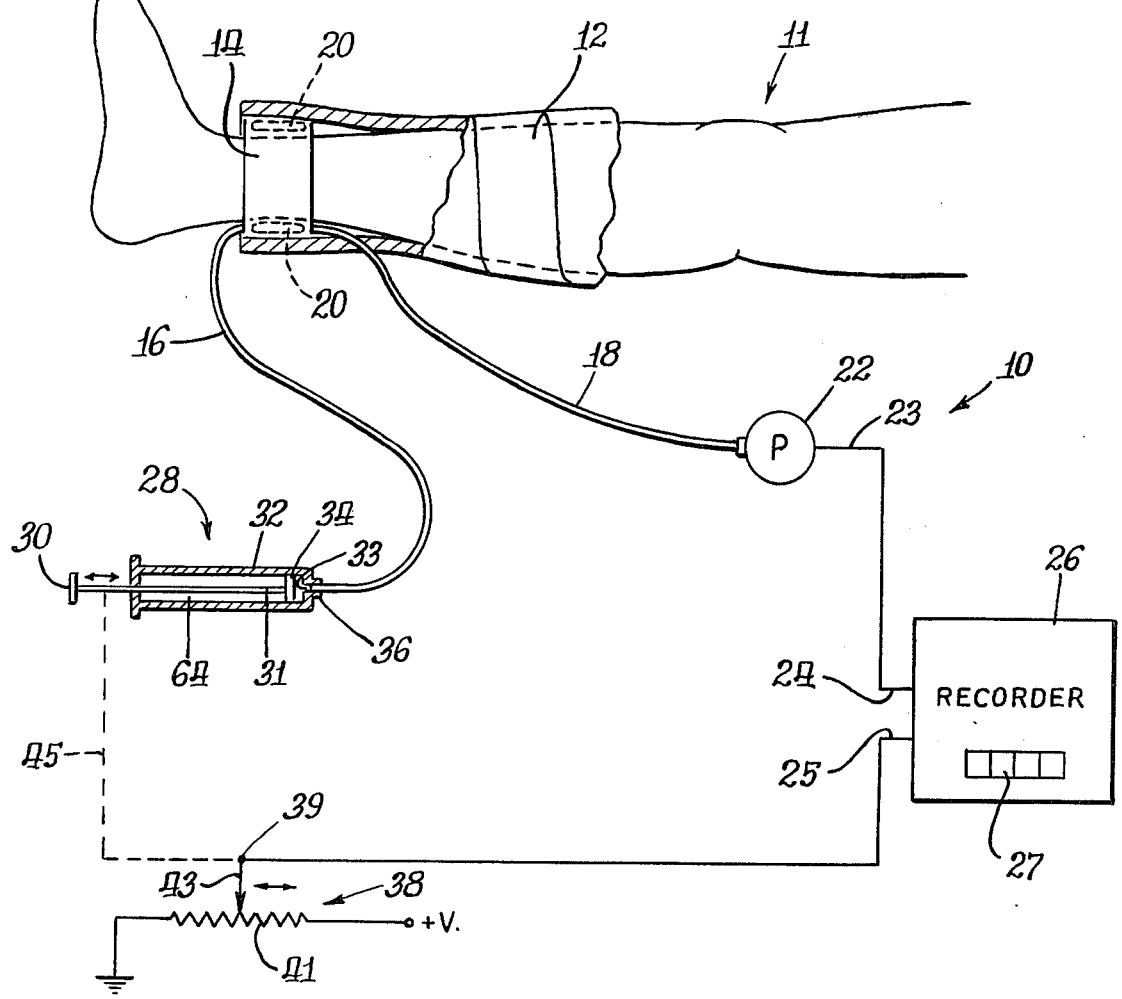
FIG. 1 is a schematic illustration of the pressure measurement apparatus of the present invention.
Figure 2:
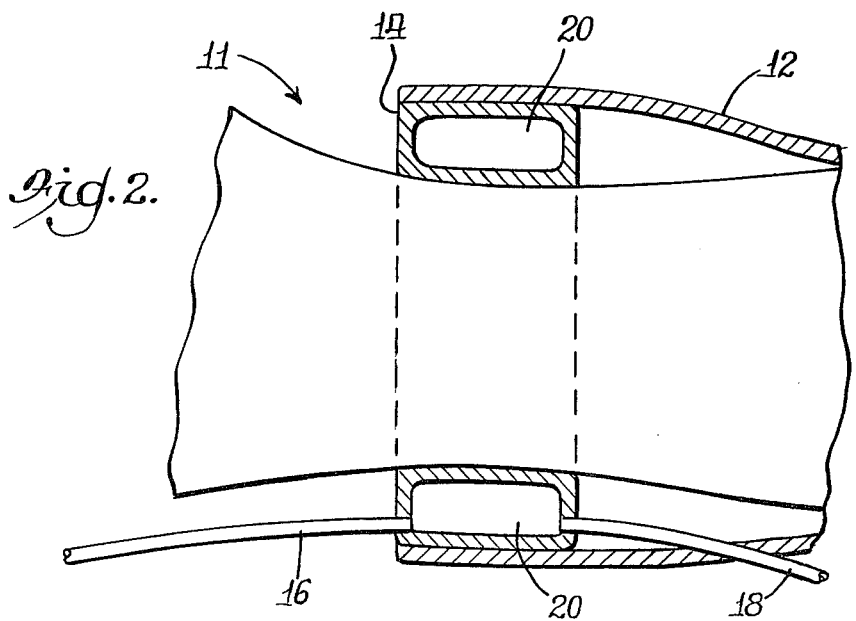
FIG. 2 is an enlarged sectional view of inflatable cuff of the apparatus of FIG. 1.

Referring to FIG. 1, the pressure measurement apparatus 10 is shown in partial schematic view as being used to determine the compressive forces applied to a leg 11 by an inflatable garment 12. Garment 12 is shown secured to leg 11 as it would appear in application for a broken leg. A flexible, pressurizable member, or cuff 14, is wrapped around the ankle of leg 11 and between inflatable garment 12 and leg 11, as most clearly seen in FIG. 2. Alternately, a smaller cuff 14 could be merely inserted between the leg and garment 12 and not wrapped all the way around the leg. A flexible input tube 16 connects the interior of cuff 14 with a syringe-like device 28. Another flexible tube 18 connects the interior of cuff 14 to a pressure transducer 22 used to measure the total pressure in cuff 14 and produce a representative signal on its output 23.

Another transducer 38 produces another electrical signal on the output 39 representative of the bias pressure introduced by device 28. The two electrical pressure signals from transducers 22 and 38 which are properly conditioned with respect to gain, off-set and linearity, are applied to inputs 24 and 25 respectively of a recorder 26. Recorder 26 either records the signals on paper for graphic extrapolation or temporarily, electronically records the signals and calculates the pressure of garment 12, and displays it on a digital readout 27.

Device 28 is used to inject air or other gas into the cuff 14 to create a bias pressure therein. As seen in FIG. 1, it comprises a syringe-like device having a plunger 34 snugly mounted for sliding movement within a cylinder 32. The plunger 34 is manually actuated by pushing or pulling a plunger handle 30 connected to plunger 34 by shaft 31. Movement of plunger 34 toward connector 36 by a preselected amount infuses a preselected amount of air through a tube 16 and into cuff 14. A check valve 33 prevents return of air from cuff 14.

Transducer 38 comprises a potentiometer resistor 41 with one end connected to ground and the other end connected to a suitable D.C. supply voltage $+V$. The output 39 is taken from the potentiometer tap 43 which is mechanically connected to plunger 34 so that it slides across resistor 41 proportionately with movement of plunger 34 by means of a suitable linkage schematically illustrated by broken line 45. As the plunger 34 moves toward connector 36, a proportionately increasing D.C. signal is produced on output 39 and applied to recorder input 25. This signal is thus representative of the amount of air injected into cuff 14 which is approximately proportioned to the increase in bias pressure in the cuff due to injections of such amount of air.

Pressure transducer 22, on the other hand, produces an electrical signal on its output 23 having an amplitude which varies proportionately with and is representative of the total pressure in cuff 14. While a variety of known types of transducers, such as a diaphragm-strain gauge type transducer, may be used for this purpose, the transducer shown in FIG. 4 and described below is preferred.

Another suitable form of transducer 22 of the present invention is one identical to transducer 38 and linked to a syringe-like device identical to device 28, except with a spring located at 64 resisting movement of plunger 34 away from connector 36. When using such a transducer, tube 18 is attached to connector 36, so that the cuff pressure pushes the plunger away from the connector, and the proportional signal produced on this potentiometer resistor is applied to input 24.

Recorder 26 receives both the bias pressure representative signal and the cuff pressure representative signal and simultaneously records both, so that there is a cuff pressure recorded for each recording of bias pressure. In accordance with one embodiment, the recorder is an ordinary x-y chart recorder which records the two signals on a strip of paper in the form of a plot, or graph, of cuff pressure versus bias pressure of the type illustrated in FIG. 3. As will be described below, from such a plot the cuff pressure component due to the compression of the garment 12 is determined by graphic extrapolation. Alternately, the signals may be temporarily stored electronically and the extrapolation calculated by a suitable computer, in which case the resultant garment pressure is displayed on readout 27.

In using the measurement apparatus 10, the cuff 14 is inserted in a deflated form between inflatable garment 12 and leg 11, either before or after garment 12 is inflated. The garment 12 is inflated to what is estimated to be the proper pressure. Device 28 is then actuated to inject cuff 14 with known amounts of air. Injection continues until after any voids between the cuff and garment have been eliminated and air spaces 20 have been fully formed, so that accurate cuff pressure measurements may be made. During injection the bias pressure representative signal and the resulting increasing cuff pressure signal are generated and recorded.

Figure 3:
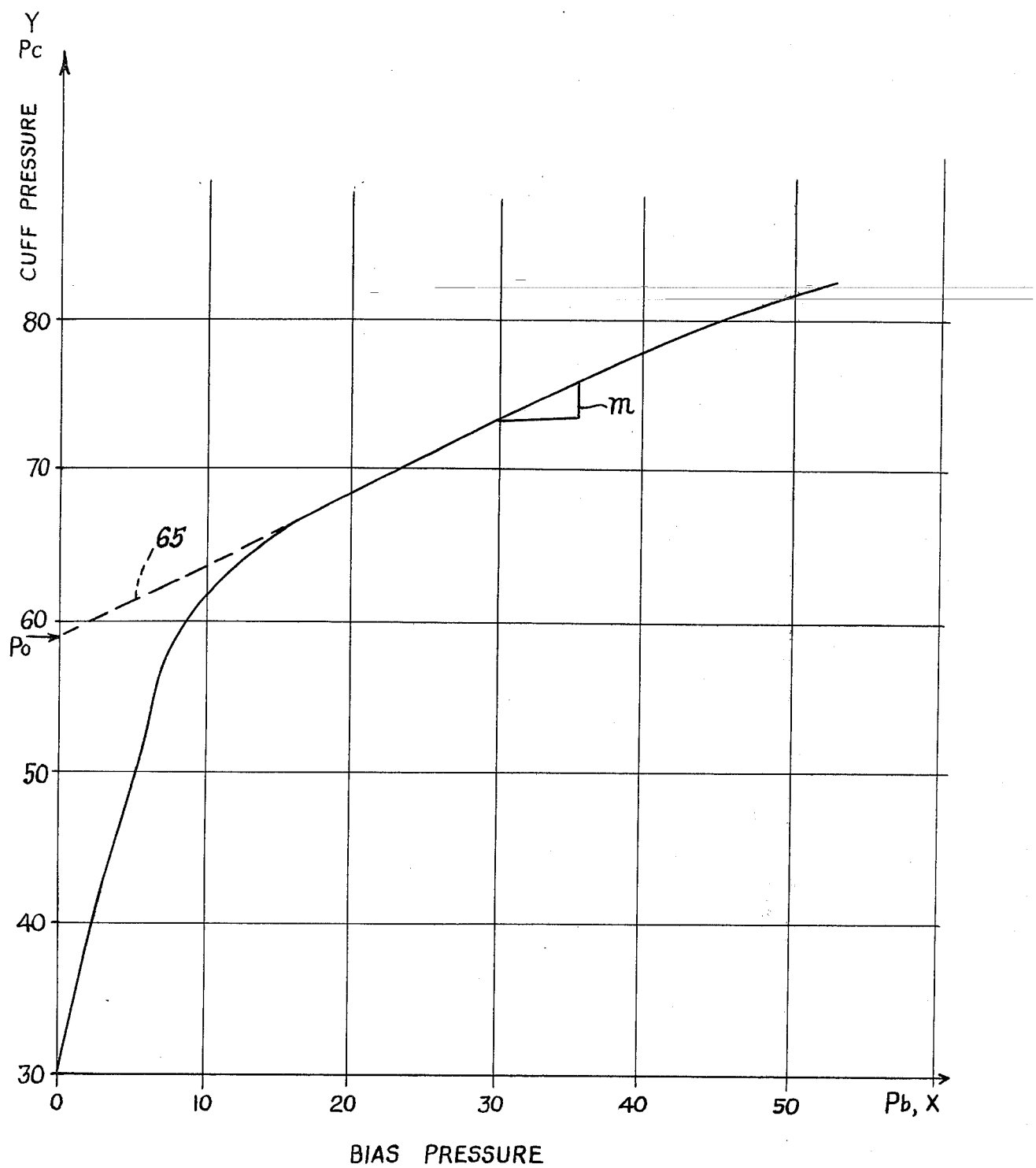
FIG. 3 is an illustrative graph of cuff pressure versus bias pressure.

Referring to FIG. 3, an illustration of the variation of cuff pressure with increases on bias pressure is shown. Units on the graph are in milimeters of mercury. When there is no air in the cuff, i.e., when bias pressure is zero, the indicated cuff compression is zero even though compression is being applied by the garment 12. This is because there is no air pressure in the cuff for the transducer to measure. After an amount of air has been injected into the cuff, such that there is bias air pressure in the cuff, the compressive forces of the garment 12 will operate on the cuff to reduce its volume and increase the pressure.

At the beginning of injection, when there is an insufficient amount of air to prevent partial collapse of the cuff and to eliminate voids, the pressure transducer records rapid increases in cuff pressure for relatively small increases in bias pressure. This is seen in FIG. 3 for bias pressure in the range of zero to ten milimeters of mercury. In this range of bias pressure it is believed that the cuff pressure is not an accurate measure of the garment pressure because of the voids and partial collapse, as described above.

However, as the bias pressure continues to increase beyond this point, the cuff pressure increases more slowly and linearly. In this range of bias pressure, the cuff pressure has two components. The first component is, of course, due to the injected air and is the bias pressure. As more air is injected, the cuff pressure will naturally increase. The other component of cuff pressure is due to the compressive force applied to the garment against the cuff which is proportional to the garment pressure. As compression increases, cuff volume decreases and cuff pressure increases. With the garment pressure constant, as is the case illustrated in FIG. 3, it is found that the cuff pressure increases more gradually but in a linear fashion.

The bias pressure of the cuff against the garment is believed to alter the garment pressure in addition to changing the cuff pressure. Thus, in order to obtain an accurate measure of the garment pressure when there is no bias pressure, the linear region of the plot is extrapolated downward to zero bias pressure to determine the theoretical cuff pressure at zero bias pressure. If the cuff pressure and bias pressure are plotted on paper by a chart recorder, the extrapolation can be done graphically as illustrated by broken-line 65 in FIG. 3 which intersects the y or cuff pressure axis at approximately 58 milimeters of mercury.

Alternately, the extrapolation can be done analytically by a suitable computer. The more gradually sloped linear portion of the plot spaced from the origin, i.e., the portion in the range of twenty to fifty milimeters of mercury, is described by the equation $Pc = mPb + Po$ where Pc is the cuff pressure, m is the slope of the linear plot, Pb is the bias pressure and Po is the theoretical cuff pressure existing when Pb equals zero. Thus, the computer need merely determine the value of m, select any point on the linear curve for values of Pc and Pb and solve for Po.

In either event, after the cuff pressure component due to the garment pressure is determined, the cuff is deflated by means of a suitable release valve. If adjustments to the garment pressure are indicated, the cuff is kept in place for a new measurement after the garment pressure is adjusted. Once the desired garment pressure is achieved, the cuff is removed, and the apparatus may be used to measure the pressure of another garment.

Figure 4:
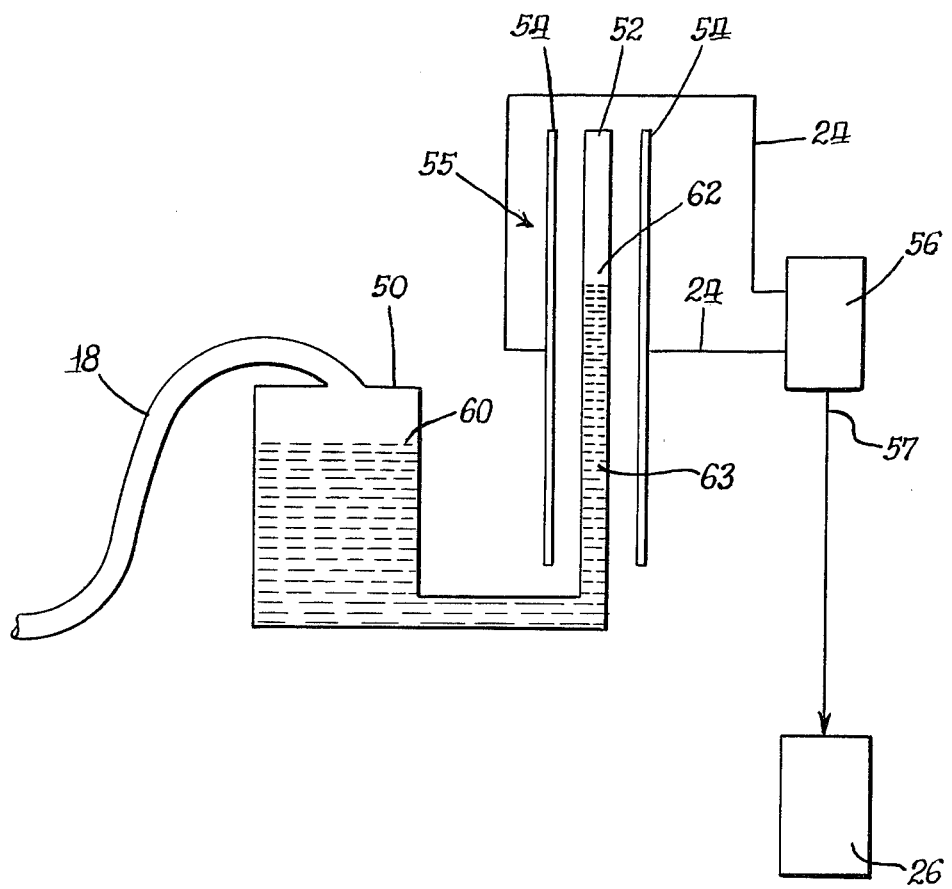
FIG. 4 is a schematic illustration of the preferred embodiment of the pressure transducer of the apparatus of FIG. 1.

Referring now to FIG. 4, a preferred form of a pressure transducer for use as pressure transducer 22 of FIG. 1 is seen to include a manometer 50 having a manometer tube 62 with manometer fluid 63 therein extending between a pair of plates 54 of a capacitor 55. The other end of the tube is connected to a fluid basin 60 which is in pneumatic communication through tube 18 with the pressure cuff 14 (not shown).

The manometer fluid level rises with increases of cuff pressure and falls with decreases in cuff pressure. A fluid is selected such as mercury, which has a dielectric constant different from that of whatever matter, such as air, is otherwise located between the plates 54. Accordingly, the capacitance of the capacitor 55 changes in accordance with movement of the manometer fluid level and cuff pressure. The use of the manometer is particularly advantageous, since it is the standard pressure measurement reference and is inherently linear and easy to zero and calibrate. The capacitor is connected to a capacitive bridge, oscillator or other circuit 56 with produces a resulting electrical signal on its output 57 representative of the cuff pressure. This signal, in turn, is connected to recorder 26.

The foregoing detailed description is given for clearness of understanding only, and no unnecessary limitations should be understood therefrom, as modifications will be obvious to those skilled in the art. For example, while a capacitor is employed in connection with the manometer of the transducer of FIG. 4, it is contemplated that the same technique could be used with an inductance coil.

I claim:

1. Apparatus for indirect measurement of the compression of an inflatable garment against a portion of a body, comprising:
   a flexible, pressurizable member adaptable for compression between the inflatable garment and the body portion;
   means for injecting the pressurizable member with a known amount of gas to produce bias pressure therein; and
   means for measuring the total pressure within the pressurizable member due to the bias pressure and the compression of the inflatable garment.

2. The apparatus of claim 1 including means for measuring the amount of gas being injected into the pressurizable member.

3. The apparatus of claim 2 in which said measuring means includes a transducer for producing an electrical signal representative of the quantity of injected gas.

4. The apparatus of claim 3 in which said injecting means comprises a syringe-like device with a cylinder connected with the pressurizable member and a plunger mounted for slidable movement within said cylinder.

5. The apparatus of claim 4 in which said transducer includes means for converting the motion of said plunger to an electrical signal representative of the amount of such movement, said amount of movement being proportional to the quantity of gas being injected.

6. The apparatus of claim 5 in which said transducer comprises a potentiometer having a slidable tap and means for moving said tap proportionately with the movement of the plunger.

7. The apparatus of claim 3 in which said total pressure measuring means includes a transducer for producing an eletrical signal representative of the total pressure.

8. The apparatus of claim 7 including means responsive to the electrical signals for producing a plot of one of said signals versus the other signal, said plot being of a form from which the total pressure in the pressurizable member due solely to the compressive forces of the garment applied thereto can be determined by graphic extrapolation.

9. The apparatus of claim 7 including means responsive to the electrical signals for computing the total pressure in the pressurizable member due solely to the compressive forces of the garment applied thereto.

10. The apparatus of claim 7 in which said pressure measuring transducer comprises
    a syringe-like device with a plunger mounted for slidable movement within a cylinder in pneumatic communication with the flexible member; and
    means for producing an electrical signal proportional to said plunger movement, said plunger being caused to move by the pressure in said flexible member by an amount proportional thereto.

11. The apparatus of claim 10 in which said transducer includes a spring mounted to said cylinder to oppose movement of the plunger caused by the pressure of the flexible member.

12. The apparatus of claim 7 in which said transducer comprises
    an oscillator circuit,
    a variable capacitor, and
    means for varying the capacitor in accordance with changes in pressure of the flexible member, said oscillator producing an output signal which varies in accordance with the variations of said capacitor.

13. The apparatus of claim 12 in which said capacitor has two plates and said means for varying the capacitor includes a manometer with a tube having a manometer fluid therein extending between the plates and connected with the flexible member, the level of said fluid varying with varying pressure in the flexible member and the capacitance of said capacitor varying with variations in the level of the fluid in the tube.

* * * * *